United States Patent [19]

Brand et al.

[11] 4,419,353

[45] Dec. 6, 1983

[54] ISOXAZOLYL INDOLAMINES

[75] Inventors: Leonard J. Brand, Randolph; Jeffrey Nadelson, Denville, both of N.J.

[73] Assignee: Sandoz, Inc., East Hanover, N.J.

[21] Appl. No.: 351,185

[22] Filed: Feb. 22, 1982

Related U.S. Application Data

[60] Division of Ser. No. 245,188, Mar. 18, 1981, Pat. No. 4,336,379, which is a continuation-in-part of Ser. No. 196,785, Oct. 14, 1980, abandoned, which is a continuation-in-part of Ser. No. 138,872, Apr. 10, 1980, abandoned.

[51] Int. Cl.³ .................. A61K 31/40; A61K 31/42
[52] U.S. Cl. .................. 424/248.4; 424/250; 424/262; 424/272; 424/248.57
[58] Field of Search ............ 548/247; 424/272, 248.4, 424/262

[56] References Cited
U.S. PATENT DOCUMENTS 4,336,378  6/1982  Brand et al. ............ 424/272

OTHER PUBLICATIONS

Smith et al., "Hypoglycemic Action of Tryptophan,", *Chem. Abst.* 87: 16491(t), (1977).
Mohri et al., "Oxidized Indole Alkaloids", Chem. Abst. 92: 198594(n), (1980).

*Primary Examiner*—Mark L. Berch
*Assistant Examiner*—G. Hendricks
*Attorney, Agent, or Firm*—Gerald D. Sharkin; Robert S. Honor; Thomas O. McGovern

[57] ABSTRACT

This disclosure describes compounds of the formula

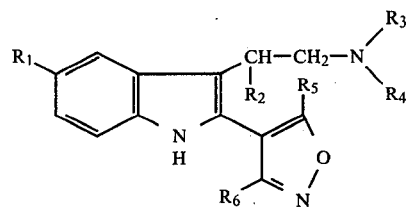

where
$R_1$ represents hydrogen, fluoro, chloro, lower alkyl having 1 to 4 carbon atoms or lower alkoxy having 1 to 4 carbon atoms, and
$R_2$ represents hydroxy, and
$R_3$ and $R_4$ each independently represent lower alkyl as defined above, or
$R_3$ and $R_4$ together with N represent

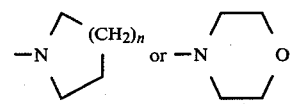

wherein
n is 1, 2 or 3, and
$R_5$ and $R_6$ each independently represent hydrogen or lower alkyl as defined above,
or a pharmaceutically acceptable acid addition salt thereof, which are useful as anti-diabetic agents, in particular as hypoglycemic agents and inhibiting or impeding post-prandial hyperglycemia.

19 Claims, No Drawings

ISOXAZOLYL INDOLAMINES

This is a division of application Ser. No. 245,188, U.S. Pat. No. 4,336,379 filed Mar. 18, 1981, which in turn is a continuation-in-part of Ser. No. 196,785, filed Oct. 14, 1980, now abandoned, which in turn is a continuation-in-part of Ser. No. 138,872, filed Apr. 10, 1980, now abandoned.

This invention relates to substituted indolamines which exhibit anti-diabetic activity. In particular, it relates to substituted isoxazolyl indolamines and pharmaceutically acceptable acid addition salts.

The compounds of this invention may be represented by the following structural formula:

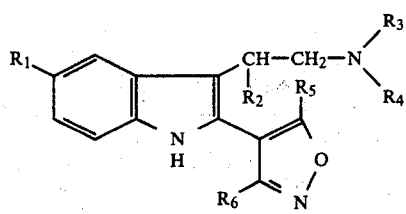

wherein $R_1$ represents hydrogen, fluoro, chloro, lower alkyl, i.e., alkyl having 1 to 4 carbon atoms, e.g., methyl, ethyl, isopropyl and the like, or lower alkoxy, i.e., alkoxy having 1 to 4 carbon atoms, e.g., methoxy, ethoxy, and the like, and $R_2$ represents hydroxy, and $R_3$ and $R_4$ each independently represent lower alkyl as defined above, or $R_3$ and $R_4$ together with N represent

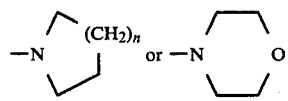

wherein n is 1, 2 or 3, and $R_5$ and $R_6$ each independently represent hydrogen or lower alkyl as defined above.

The compounds of formula (I), are prepared according to the following reaction scheme:

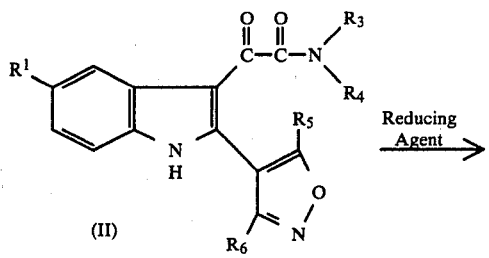

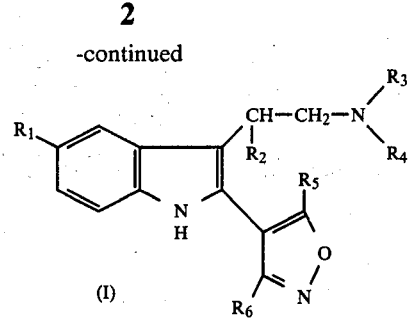

$R_1$, $R_2$, $R_3$, $R_4$, $R_5$ and $R_6$ are as defined above.

The compounds of formula (I) are prepared by reducing a compound of the formula (II) in the presence of an inert atmosphere, e.g., nitrogen, helium or argon, preferably nitrogen, with a reducing agent such as lithium aluminum hydride, or diborane, preferably lithium aluminum hydride. The reaction is carried out in the presence of an inert organic solvent, and although the particular solvent employed is not critical, the preferred solvents include an ether such as diethylether, dioxane or tetrahydrofuran, the latter being especially preferred. The temperature of the reaction may be critical, and it is preferred that the reaction be run at a temperature of from about 10° to 30° C., preferably 20° to 25° C. The reaction is run from about 1 to 12 hours, preferably from about 2 to 5 hours. The product is recovered using conventional techniques, e.g., crystallization.

The compounds of formula (II) are prepared according to the following reaction scheme:

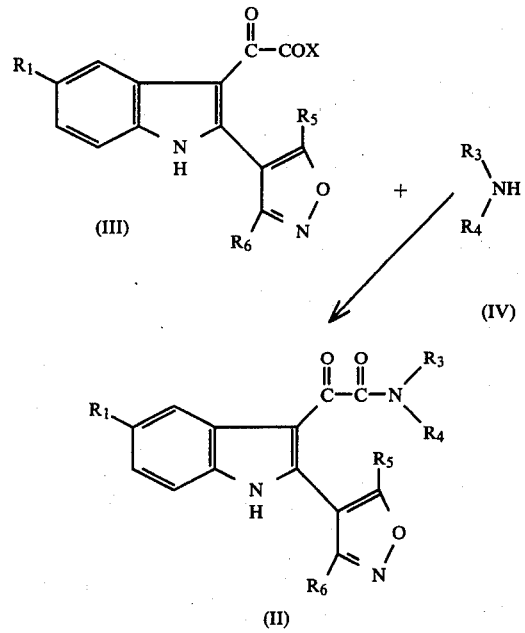

where X represents chloro or bromo, and $R_1$, $R_3$, $R_4$, $R_5$ and $R_6$ are as defined above.

The compounds of formula (II) are prepared by treating a compound of the formula (III) with a compound of the formula (IV) in the presence of a solvent. Although the particular solvent employed is not critical, the preferred solvents include water, an excess of a compound of the formula (IV) or an ether such as diethylether dioxane or tetrahydrofuran, or an aromatic hydrocarbon such as benzene, toluene and the like, preferably the combination of water, diethylether and excess compound of formula (IV). The temperature of the reaction is not critical, but it is preferred that the reaction be run from about −10° to 50° C., preferably from about 20° to 30° C. The reaction is run from about 30 minutes to 4 hours, preferably from about 1 to 2 hours. The product is recovered using conventional techniques e.g., filtration.

The compounds of formula (III) are prepared in accordance with the following reaction scheme:

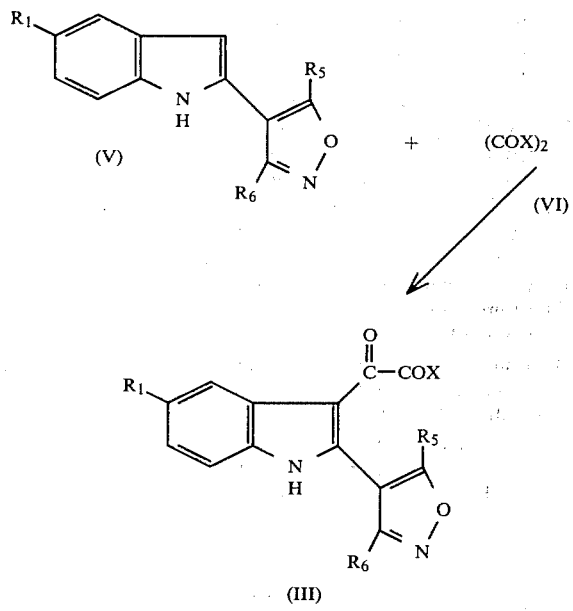

where X, R₁, R₅ and R₆ are as defined above.

The compounds of formula (III) are prepared by treating a compound of the formula (V) with a compound of the formula (VI), namely oxalyl chloride or oxalyl bromide, in the presence of an inert organic solvent. Although the particular solvent employed is not critical, the preferred solvents include an ether such as diethylether, dioxane or tetrahydrofuran, or an aromatic hydrocarbon such as benzene, toluene and the like, preferably diethylether. The temperature of the reaction is not critical, but it is preferred that the reaction be run at a temperature of from about −10° to 50° C., preferably from about 20° to 30° C. The reaction is run from about 1 to 12 hours, preferably from about 3 to 6 hours. The product may be recovered by conventional techniques, however, in this case, it is not isolated instead the compounds of formula (III) are employed in situ as a starting materials in the preparation of compounds (II).

The compounds of formula (V) are prepared in accordance with the following reaction scheme:

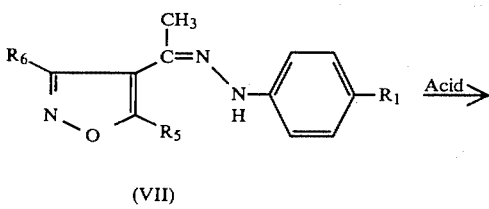

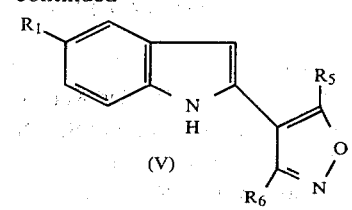

where R₁, R₅ and R₆ are as defined above.

The compounds of formula (V) are prepared by cyclizing a compound of the formula (VII) with an acid, such as acetic acid, p-toluenesulfonic acid or polyphosphoric acid, the latter being especially preferred in the presence of an inert solvent. Although the particular solvent employed is not critical, the preferred solvents include the aromatic hydrocarbons such as benzene, toluene and the like, or an excess of the acid utilized above, the latter being especially preferred. The temperature of the reaction is not critical, but it is preferred that the reaction be run from about 70° to 150° C., preferably from about 105° to 120° C. The reaction is run from about 1 to 12 hours, preferably from about 3 to 6 hours. The product is recovered using conventional techniques, e.g., filtration.

The compounds of formula (VII) are prepared according to the following reaction scheme:

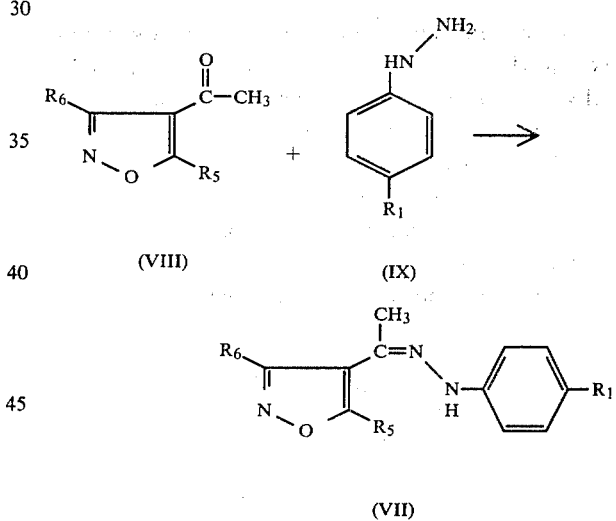

where R₁, R₅ and R₆ are as defined above.

The compounds of formula (VII) are prepared by treating a compound of the formula (VIII) with a compound of the formula (IX) in the presence of an inert organic solvent and an acid catalyst such as p-toluenesulfonic acid, polyphosphoric acid or sulfuric acid, preferably p-toluenesulfonic acid. The particular solvent employed is not critical, but it is preferred that the reaction be run in the presence of the lower alkanols, e.g., methanol, ethanol and the like, or the aromatic hydrocarbons such as benzene, toluene and the like, preferably, however, ethanol. The temperature of the reaction is not critical, but it is preferred that the reaction be run from about 0° to 100° C., preferably from about 20° to 35° C. The reaction is run from about 12 to 72 hours, preferably from about 36 to 52 hours. The product is recovered using conventional techniques, e.g., filtration.

Another aspect of this invention and the preferred method of preparing the compounds of formula (V) in which $R_5$ represents ethyl may be illustrated by the following reaction scheme.

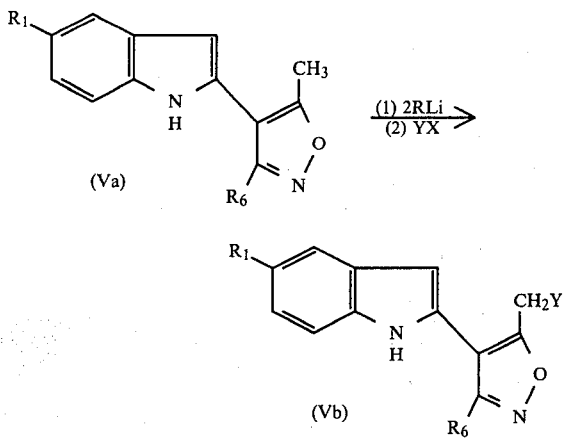

where
RLi represents an alkyl lithium,
Y represents straight chain lower alkyl having 1 to 4 carbon atoms,
X represents chloro, bromo or iodo, and
$R_1$ and $R_6$ are as defined above.

The compounds of formula (Vb) are prepared by first reacting a compound of the formula (Va) with two equivalents of an alkyl lithium in the presence of an organic co-solvent. Although the particular alkyl lithium employed is not critical, it is preferred that the reaction be run in t-butyl lithium or n-butyl lithium the latter being especially preferred. The reaction is preferably carried out in the presence of an ether such as diethylether, tetrahydrofuran or dioxane in combination with an aliphatic hydrocarbon such as pentane, hexane and the like, especially tetrahydrofuran and hexane. The temperature of this reaction is not critical, but it is preferred that the reaction be run at a temperature of from about $-75°$ to $-40°$ C. preferably from about $-60°$ to $-50°$ C. The reaction is run from about 10 minutes to 60 minutes preferably from about 25 to 40 minutes.

The resulting product is not isolated but instead is then reacted with an alkyl halide such as methylbromide, methyliodide and the like preferably methyliodide in the presence of an inert organic solvent to form compounds (Vb). The preferred iunert organic solvent includes the ethers such as diethylether, tetrahydrofuran or dioxane or the aromatic hydrocarbons such as benzene, toluene and the like, preferably tetrahydrofuran. The temperature of the reaction is not criticl but it is preferred that the reaction be run at a temperature of from about $-75°$ to $-40°$ C., preferably from about $-60°$ to $-50°$ C. The reaction is run from about 1 to 8 hours preferably from about 3 to 6 hours. The resulting product may be recovered by conventional techniques e.g. filtration followed by evaporation. It should be noted that the compounds of the formula (Vb) are precursors and may be employed in accordance with the reaction scheme set out on page 4 of the Specification to obtain the compounds of formula (III) wherein $R_5$ represents ethyl.

Many of the compounds of formulae (IV), (VI), (VIII), and (IX) are known and may be prepared by methods described in the literature. The compounds of formulae (IV), (VI), (VII), and (IX) not specifically described may be prepared by analogous methods from known starting materials.

It will be understood that the compounds of formula (I) may exist in the form of optically active isomers and can be separated and recovered by conventional techniques, and that such isomeric forms are included within the scope of the invention.

The compounds of formula (I), and their pharmaceutically acceptable salts, are useful because they exhibit pharmacological activity in animals. In particular, the compounds of formula (I) are useful in the treatment of diabetes as hypoglycemic agents and inhibiting or impeding post-prandial hyperglycemia.

The compounds of formula (I) are useful in the treatment of diabetes as hyupoglycemic agents as indicated by the lowering of blood glucose in 6 to 8 week old male Royah Hart mice weighing 30 to 35 grams which are fasted in groups of 5 for 16 hours and then are given an initial dose of 50 to 200 milligrams per kilogram of animal body weight of the compound orally. Two hours after the test compound is administered the mice are anesthetized with 85 milligrams per kilogram of animal body weight of sodium hexobarbital and five minutes later blood is collected via cardiac puncture. The blood samples are placed in an autoanalyzer cup containing 0.025 milliliters of heparin (1,000 units per milliliter); and the samples are capped, shaken and stored in ice. The glucose level is determined by the autoanalyzer potassium ferric cyanide N-2b method and these glucose levels are then compared with the glucose levels of the control group which receives orally 0.5% carboxymethyl cellulose and is run concurrently. To validate this experiment, a known hypoglycemic standard is included each time the test is run.

The compounds of formula (I) are also useful in treatment of diabetes by inhibiting or impeding post-prandial hyperglycemia as indicated by a lowering of the blood sugar levels in male Wistar rates after an oral starch load. In this test male Wistar rats in groups of 5 which are fasted for 16 hours are given an initial dose of from 25 to 200 mg/kg. p.o. of the test compound. One hour later the rats are given 1.0 grams per kilogram of animal body weight of cooked starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliters). The heparinizied blood is used to determine the blood sugar level with an autoanalyzer. The blood sugar content is compared to the control group which receives 0.5% carboxymethyl cellulose and an oral starch load and are run concurrently.

For both the hypoglycemic and inhibiting post-prandial hyperglycemia use, the compounds of formula (I) and their non-toxic, pharmaceutically acceptable salts may be administered orally or parenterally as such as admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., magnesium stearate, steric acid and talc. The tablets may be coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination wiht the carrier or adjuvant.

The hypoglycemic effective amount of active ingredient employed in the treatment of diabetes may vary depending on the particular compound employed, the mode of administration and the severity of the condition being treated. However, in general satisfactory results in the treatment of diabetes are obtained when a compound of formula (I), or a pharmaceutically acceptable salt thereof, is administered at a dialy dosage of from about 5 milligrams to about 800 milligrams per kilogram of animal body weight, preferably given orally and in divided doses two or four times a day, or in sustained release form. For most large mammals, the total daily dosage is from about 50 milligrams to about 2000 milligrams. Unit dosage forms suitable for internal use comprise from about 12.5 milligrams to about 2000 milligrams, more usually 12.5 to 1000 milligrams, of the active compound in intimate admixture with a solid or liquid, pharmaceutically acceptable carrier.

The effective amount of active ingredient for inhibiting post-prandial hyperglycemia employed in the treatment of diabetes may vary depending on the particular compound employed, the mode of administration and the severity of the condition being treated. However, in general satisfactory results in the treatment of diabetes are obtained when a compound of formula (I), or a pharmaceutically acceptable salt thereof, is administered at a dialy dosage of from about 5 milligrams to about 80 milligrams per kilogram of animal body weight, preferably given orally and in divided doses two to four times a day, or in sustained release form. For most large mammals, the total daily dosage is from about 25 milligrams to about 1000 milligrams, preferably given at mealtime as conventional in treatments with substances having such activity, e.g., three times a day, particularly before a carbohydrate-rich meal.

The compounds of formula (I) may be similarly administered in the form of their non-toxic pharmaceutically acceptable acid addition salts. Such salts possess the same order of activity as the free base and are readily prepated by reacting the compound with a pharmaceutically acceptable acid by conventional techniques, and accordingly are included within the scope of this invention. Representative of the inorganic salts are the hydrochloride, hydrobromide, hydroiodide, phosphate (including hydrogen phosphate), metaphosphate, and sulfate (including hydrogne sulfate). Representative examples of the organic salts are the acetate, maleate, fumarate and the like.

Tablets and capsules containing the ingredients indicated below may be prepared by conventional techniques and are useful in treating diabetes, at a dose of one tablet or capsule, 2 to 4 times a day.

| Ingredients | Weight (mg.) tablet | capsule |
|---|---|---|
| α-(dimethylaminomethyl)-2-(3-ethyl-5-methyl-4-isoxazolyl)-1H—indole-3-methanol | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 | 500 |

EXAMPLE 1

1-(3-ethyl-5-methyl-4-isoxazolyl)-1-ethanone phenyl hydrazone

A mixture of 61.1 g. (0.4 mole) of 4-acetyl-3-ethyl-5-methyl-isoxazole, 39.4 ml. (0.4 mole) of phenyl hydrazine and 500 mg. toluenesulfonic acid in 400 ml. ethanol is stirred at room temperature for 48 hours. The resulting solid is filtered and washed with cold ether to give 1-(3-ethyl-5-methyl-4-isoxazolyl)-1-ethanone phenyl hydrazone; m.p. 72° to 75° C.

Following the above procedure and using in place of 4-acetyl-3-ethyl-5-methyl isoxazole an equivalent amount of (a) 4-acetyl-3-ethyl-isoxazole,
(b) 4-acetyl-3,5-diethyl-isoxazole,
(c) 4-acetyl-3-ethyl-5-isopropyl-isoxazole,
(d) 4-acetyl-3-ethyl-5-t-butyl-isoxazole,
(e) 4-acetyl-3,5-dimethyl-isoxazole,
(f) 4-acetyl-5-methyl-isoxazole,
(g) 4-acetyl-5-methyl-3-propyl-isoxazole, or
(h) 4-acetyl-5-methyl-3-t-butyl-isoxazole
(i) 4-acetyl-5-ethyl-3-methyl-isoxazole
(j) 4-acetyl-3-isopropyl-5-methyl-isoxazole
there is obtained (a) 1-(3-ethyl-4-isoxazolyl)-1-ethanone phenyl hydrazone,
(b) 1-(3,5-diethyl-4-isoxazolyl)-1-ethanone phenyl hydrazone,
(c) 1-(3-ethyl-5-isopropyl-4-isoxazolyl)-1-ethanone phenyl hydrazone,
(d) 1-(3-ethyl-5-t-butyl-4-isoxazolyl)-1-ethanone phenyl hydrazone,
(e) 1-(3,5-dimethyl-4-isoxazolyl)-1-ethanone phenyl hydrazone,
(f) 1-(5-methyl-4-isoxazolyl)-1-ethanone phenyl hydrazone,
(g) 1-(5-methyl-3-propyl-4-isoxazolyl)-1-ethanone phenyl hydrazone, or
(H) 1-(5-methyl-3-t-butyl-4-isoxazolyl)-1-ethanone phenyl hydrazone, respectively.
(i) 1-(5-ethyl-3-methyl-4-isoxazolyl)-1-ethanone-phenyl hydrazone,
(j) 1-(3-isopropyl-5-methyl-4-isoxazolyl)-1-ethanone-phenyl hydrazone Again, following the above procedure and using in place of phenyl hydrazine an equivalent amount of
(k) p-fluorophenyl hydrazine,
(l) p-tolyl hydrazine, or
(m) p-anisyl hydrazine
there is obtained
(k)    1-(3-ethyl-5-methyl-4-isoxazolyl)-1-ethanone-p-fluorophenyl hydrazine,
(l) 1-(3-ethyl-5-methyl-4-isoxazolyl)-1-ethanoe-p-tolyl hydrazone, or
(m) 1-(3-ethyl-5-methyl-4-isoxazolyl)-1-ethanone-p-anisyl hydrazone, respectively.

Again following the procedure set out in Example 1 and using in place of 4-acetyl-3-ethyl-5-methyl-isoxazole an equivalent amount of
(s) 4-acetyl-3,5-dimethyl-isoxazole, or
(t) 4-acetyl-5-ethyl-3-methyl-isoxazole
and using in place of phenyl hydrazine an equivalent amount of p-fluorophenyl hydrazine there is obtained:
(s)    1-(3,5-dimethyl-4-isoxazolyl)-1-ethanone-p-fluorophenyl hydrazone, or
(t)    1-(5-ethyl-3-methyl-4-isoxazolyl)-1-ethanone-p-fluorophenyl hydrazone.

EXAMPLE 2

2-(3-ethyl-5-methyl-4-isoxazolyl)-indole

To 1350 grams of polyphosphoric acid at 100° to 110° C. there is added portionwise 74.5 g. (0.307 mole) of 1-(3-ethyl-5-methyl-4-isoxazolyl)-1-ethanone phenyl hydrazone while maintaining the temperature between 105° C. and 115° C. After addition is complete, the mixture is stirred at 100° to 110° C. for 3 hours. The mixture is then poured onto ice and water and the resulting gum extracted into methylene chloride. The methylene chloride is decolorized, dried over anhydrous magnesium sulfate, filtered and evaporated in vacuo to give 2-(3-ethyl-5-methyl-4-isoxazolyl)-indole.

Following the above procedure and using in place of 1-(3-ethyl-5-methyl-4-isoxazolyl)-1-ethanone phenyl hydrazone an equivalent amount of
(a) 1-(3-ethyl-4-isoxazolyl)-1-ethanone phenyl hydrazone,
(b) 1-(3,5-diethyl-4-isoxazolyl)-1-ethanone phenyl hydrazone,
(c)    1-(3-ethyl-5-isopropyl-4-isoxazolyl)-1-ethanone phenyl hydrazone,
(d) 1-(3-ethyl-5-t-butyl-4-isoxazolyl)-1-ethanone phenyl hydrazone,
(e) 1-(3,5-dimethyl-4-isoxazolyl)-1-ethanone phenyl hydrazone,
(f) 1-(5-methyl-4-isoxazolyl)-1-ethanone phenyl hydrazone,
(g)    1-(5-methyl-3-propyl-4-isoxazolyl)-1-ethanone phenyl hydrazone,
(h)    1-(5-methyl-3-t-butyl-4-isoxazolyl)-1-ethanone phenyl hydrazone,
(i) 1-(5-ethyl-3-methyl-4-isoxazolyl)-1-ethanone phenyl hydrazone
(j)    1-(3-isopropyl-5-methyl-4-isoxazolyl)-1-ethanone phenyl hydrazone
(k)    1-(3-ethyl-5-methyl-4-isoxazolyl)-1-ethanone-p-fluorophenyl hydrazone,
(l) 1-(3-ethyl-5-methyl-4-isoxazolyl)-1-ethanone-p-tolyl hydrazone or
(m) 1-(3-ethyl-5-methyl-4-isoxazolyl)-1-ethanone-p-anisyl hydrazone
there is obtained
(a) 2-(3-ethyl-4-isoxazolyl)-indole,
(b) 2-(3,5-diethyl-4-isoxazolyl)-indole,
(c) 2-(3-ethyl-5-isopropyl-4-isoxazolyl)-indole,
(d) 2-(3-ethyl-5-t-butyl-4-isoxazolyl)-indole,
(e) 2-(3,5-dimethyl-4-isoxazolyl)-indole,
(f) 2-(5-methyl-4-isoxazolyl)-indole,
(g) 2-(5-methyl-3-propyl-4-isoxazolyl)-indole,
(h) 2-(5-methyl-3-t-butyl-4-isoxazolyl)-indole,
(i) 2-(5-ethyl-3-methyl-4-isoxazolyl)-indole
(j) 2-(3-isopropyl-5-methyl-4-isozazolyl)-indole
(k) 5-fluoro-2-(3-ethyl-5-methyl-4-isoxazolyl)-indole,
(l) 5-methyl-2-(3-ethyl-5-methyl-4-isoxazolyl)-indole, or
(m)    5-methoxy-2-(3-ethyl-5-methyl-4-isoxazolyl)-indole, respectively.

Again, following the procedure set out in Example 2 and using in place of 1-(3-ethyl-5-methyl-4-isoxazolyl)-1-ethanone phenyl hydrazone an equivalent amount of
(s)    1-(3,5-dimethyl-4-isoxazolyl)-1-ethanone-p-fluorophenyl hydrazone, or
(t)    1-(5-ethyl-3-methyl-4-isoxazolyl)-1-ethanone-p-fluorophenyl hydrazone,
there is obtained
(s) 5-fluoro-2-(3,5-dimethyl-4-isoxazolyl)-indole, or
(t) 5-fluoro-2-(5-ethyl-3-methyl-4-isoxazolyl)-indole.

EXAMPLE 3

2-(3-ethyl-5-methyl-4-isoxazolyl)-3-indole-glyoxylchloride

A mixture of 163 g. (0.72 mole) of 2-(3-ethyl-5-methyl-4-isoxazolyl)-indole and 3 liters of ether are cooled to 0° to 10° C. and 61.6 ml. (0.72 mole) of oxalye chloride in 450 ml. of ether is added dropwise, maintaining the temperature at 0° to 10° C. during the addition. The cooling bath is removed and the mixture allowed to warm to room temperature. After 1½ hours, more starting material is still present and 3.1 ml. (0.0362 mole) of oxalyl chloride is added and the mixture stirred for additional 1½ hours longer. Total stirring at room temperature is 3 hours. The solvent is evaporated in vacuo to give a solid residue. The residue is suspended in ether and evaporated twice more to give 2-(3-ethyl-5-methyl-4-isoxazolyl)-3-indoleglyoxyl chloride.

Following the above procedure and using in place of 2-(3-ethyl-5-methyl-4-isoxazolyl)-indole an equivalent amount of
(a) 2-(3-ethyl-4-isoxazolyl)-indole,
(b) 2-(3,5-diethyl-4-isoxazolyl)-indole,
(c) 2-(3-ethyl-5-isopropyl-4-isoxazolyl)-indole,
(d) 2-(3-ethyl-5-t-butyl-4-isoxazolyl)-indole,
(e) 2-(3,5-dimethyl-4-isoxazolyl)-indole,
(f) 2-(5-methy-4-isoxazolyl)-indole,
(g) 2-(5-methyl-3-propyl-4-isoxazolyl)-indole,
(h) 2-(5-methyl-3-t-butyl-4-isoxazolyl)-indole,
(i) 2-(5-ethyl-3-methyl-4-isozazolyl)-indole,
(j) 2-(3-isopropyl-5-methyl-4-isoxazolyl)-indole
(k) 5-fluoro-2-(3-ethyl-5-methyl-4-isoxazolyl)-indole,
(l)    5-methyl-2-(3-ethyl-5-methyl-(4-isoxazolyl)-indole, or
(m) 5-methoxy-2-(3-ethyl-5-methyl-4-isoxazolyl)-indole
there is obtained
(a) 2-(3-ethyl-4-isoxazolyl)-3-indoleglyoxyl chloride,
(b) 2-(3,5-diethyl-4-isoxazolyl)-3-indoleglyoxyl chloride,
(c) 2-(3-ethyl-5-isopropyl-4-isoxazolyl)-3-indoleglyoxyl chloride,
(d)    2-(3-ethyl-5-t-butyl-4-isoxazolyl)-3-indoleglyoxyl chloride, (e) 2-(3,5-dimethyl-4-isoxazolyl)-3-indoleglyoxyl chloride,
(f) 2-(5-methyl-4-isoxazolyl)-3-indoleglyoxyl chloride,
(g) 2-(5-methyl-3-propyl-4-isoxazolyl)-3-indoleglyoxyl chloride,
(h) 2-(5-methyl-3-t-butyl-4-isoxazolyl)-3-indoleglyoxyl chloride,
(i) 2-(5-ethyl-3-methyl-4-isoxazolyl)-3-indoleglyoxyl chloride,
(j) 2-(3-isopropyl-5-methyl-4-isoxazolyl)-3-indoleglyoxyl chloride
(k) 5-fluoro-2-(3-ethyl-5-methyl-4-isoxazolyl)-3-indoleglyoxyl chloride,
(l) 5-methyl-2-(3-ethyl-5-methyl-4-isoxazolyl)-3-indoleglyoxyl chloride, or
(m) 5-methoxy-2-(3-ethyl-5-methyl-4-isoxazolyl)-3-indoleglyoxyl chloride, respectively.

Again, following the procedure set out in Example 3, and using in place of 2-(3-ethyl-5-methyl-4-isoxazolyl)-indole an equivalent amount of
(s) 5-fluoro-2-(3,5-dimethyl-4-isoxazolyl)-indole, or
(t) 5-fluoro-2-(5-ethyl-3-methyl-4-isoxazolyl)-indole
there is obtained
(s) 5-fluoro-2-(3,5-dimethyl-4-isoxazolyl)-3-indoleglyoxyl chloride, or
(t) 5-fluoro-2-(5-ethyl-3-methyl-4-isoxazolyl)-3-indoleglyoxyl chloride.

EXAMPLE 4

N,N-dimethyl-2-(3-ethyl-5-methyl-4-isoxazolyl)-3-indole-glyoxylamide 79.0 g. (0.250 mole) of 2-(3-ethyl-5-methyl-4-isoxazolyl)-3-indoleglyoxyl chloride is added portionwise to a 0° to 10° C. cooled mixture of 1200 ml. of 40% aqueous dimethylamine and 1000 ml. of ether. The resulting mixture is stirred for 1 hour without an ice bath and then filtered. The solid is then washed well with water and with three portions of cold ether to give N,N-dimethyl-2-(3-ethyl-5-methyl-4-isoxazolyl)-3-indoleglyoxylamide; m.p. 212° to 215° C.

Following the above procedure and using in place of 2-(3-ethyl-5-methyl-4-isoxazolyl)-3-indoleglyoxyl chloride an equivalent amount of
(a) 2-(3-ethyl-4-isoxazolyl)-3-indoleglyoxyl chloride,
(b) 2-(3,5-diethyl-4-isoxazolyl)-3-indoleglyoxyl-chloride,
(c) 2-(3-ethyl-5-isopropyl-4-isoxazolyl)-3-indoleglyoxyl chloride,
(d) 2-(3-ethyl-5-t-butyl-4-isoxazolyl)-3-indoleglyoxyl chloride,
(e) 2-(3,5-dimethyl-4-isoxazolyl)-3-indoleglyoxyl chloride,
(f) 2-(5-methyl-4-isoxazolyl)-3-indoleglyoxyl chloride,
(g) 2-(5-methyl-3-propyl-4-isoxazolyl)-3-indoleglyoxyl chloride,
(h) 2-(5-methyl-3-t-butyl-4-isoxazolyl)-3-indoleglyoxyl chloride,
(i) 2-(5-methyl-3-methyl-4-isoxazolyl)-3-indoleglyoxyl chloride,
(j) 2-(3-isopropyl-5-methyl-4-isoxazolyl)-3-indoleglyoxyl chloride
(k) 5-fluoro-2-(3-ethyl-5-methyl-4-isoxazolyl)-3-indoleglyoxyl chloride,
(l) 5-methyl-2-(3-ethyl-5-methyl-4-isoxazolyl)-3-indoleglyoxyl chloride, or
(m) 5-methoxy-2-(3-ethyl-5-methyl-4-isoxazolyl)-3-indoleglyoxyl chloride
there is obtained
(a) N,N-dimethyl-2-(3-ethyl-4-isoxazolyl)-3-indoleglyoxylamide,
(b) N,N-dimethyl-2-(3,5-diethyl-4-isoxazolyl)-3-indoleglyoxylamide,
(c) N,N-dimethyl-2-(3-ethyl-5-isopropyl-4-isoxazolyl)-3-indoleglyoxylamide,
(d) N,N-dimethyl-2-(3-ethyl-5-t-butyl-4-isoxazolyl)-3-indoleglyoxylamide,
(e) N,N-dimethyl-2-(3,5-dimethyl-4-isoxazolyl)-3-indoleglyoxylamide,
(f) N,N-dimethyl-2-(5-methyl-4-isoxazolyl)-3-indoleglyoxylamide,
(g) N,N-dimethyl-2-(5-methyl-3-propyl-4-isoxazolyl)-3-indoleglyoxylamide,
(h) N,N-dimethyl-2-(5-methyl-5-t-butyl-4-isoxazolyl)-3-indoleglyoxylamide,
(i) N,N-dimethyl-2-(5-ethyl-3-methyl-4-isoxazolyl)-3-indoleglyoxylamide,
(j) N,N-dimethyl-2-(3-isopropyl-5-methyl-4-isoxazolyl)-3-indoleglyoxylamide
(k) 5-fluoro-N,N-dimethyl-2-(3-ethyl-5-methyl-4-isoxazolyl)-3-indoleglyoxylamide,
(l) 5-methyl-N,N-dimethyl-2-(3-ethyl-5-methyl-4-isoxazolyl)-3-indoleglyoxylamide, or
(m) 5-methoxy-N,N-dimethyl-2-(3-ethyl-5-methyl-4-isoxazolyl)-3-indoleglyoxylamide, respectively.

Also following the above procedure and using in place of dimethylamine an equivalent amount of
(n) diethylamine,
(o) morpholine,
(p) pyrrolidine, or
(q) piperidine
there is obtained
(n) N,N-diethyl-2-(3-ethyl-5-methyl-4-isoxazolyl)-3-indoleglyoxylamide,
(o) 2-(3-ethyl-5-methyl-4-isoxazolyl)-3-indoleglyoxyl-morpholide,
(p) 2-(3-ethyl-5-methyl-4-isoxazolyl)-3-indoleglyoxyl-pyrrolidide, or
(q) 2-(3-ethyl-5-methyl-4-isoxazolyl)-3-indoleglyoxyl-piperidide, respectively.

Following the procedure of Example 4 and using in place of 2-(3-ethyl-5-methyl-4-isoxazolyl)-3-indoleglyoxyl chloride an equivalent amount of 5-fluoro-2-(3-ethyl-5-methyl-4-isoxazolyl)-3-indoleglyoxylchloride
and in place of dimethylamine an equivalent amount of pyrrolidine there is obtained.
(r) 5-fluoro-2-(3-ethyl-5-methyl-isoxazolyl)-3-indole glyoxylpyrrolidide.

Again, following the procedure of Example 4 and using in place of 2-(3-ethyl-5-methyl-4-isoxazolyl)-3-indoleglyoxyl chloride an equivalent amountof
(s) 5-fluoro-2-(3,5-dimethyl-4-isoxazolyl)-3-indoleglyoxyl chloride, or
(t) 5-fluoro-2-(5-ethyl-3-methyl-4-isoxazolyl)-3-indoleglyoxyl chloride
there is obtained
(s) 5-fluoro-N,N-dimethyl-2-(3,5-dimethyl-4-isoxazolyl)-3-indoleglyoxylamide, or
(t) 5-fluoro-N,N-dimethyl-2-(5-ethyl-3-methyl-4-isoxazolyl)-3-indoleglyoxylamide.

Also following the procedure of Example 4 and using in place of 2-(3-ethyl-5-methyl-4-isoxazolyl)-3-indoleglyoxyl chloride an equivalent amount of starting materials (t) and (s) respectively and in place of dimethylamine an equivalent amount of pyrrolidine there is obtained (u) 5-fluoro-2-(5-ethyl-3-methyl-4-isoxazolyl)-3-indoleglyoxylpyrrolidide, or
(v) 5-fluoro-2-(3,5-dimethyl-4-isoxazolyl)-3-indoleglyoxylpyrrolidide.

EXAMPLE 5

α-(dimethylaminomethyl)-2-(3-ethyl-5-methyl-4-isoxazolyl)-1H-indole-3-methanol

To a suspension of 9.9 g. (0.26 mole) of lithium aluminum hydride and 950 ml. tetrahydrofuran under nitrogen there is added 21.0 g. (0.065 mole) of N,N-dimethyl-2-(3-ethyl-5-methyl-4-isoxazolyl)-3-indoleglyoxylamide in 735 ml. of tetrahydrofuran, while maintaining the temperature between 20° to 25° C. After addition is complete, the mixture is stirred at room temperature for 5 hours then cooled to 0° and quenched by the addition dropwise of 20 ml. of water in 180 ml. of tetrahydrofuran. The resulting solids are filtered and the tetrahydrofuran dried over anhydrous magnesium sulfate, filtered and evaporated. The residue is recrystallized from ethanol to give α-(dimethylaminomethyl)-2-(3-ethyl-5-methyl-4-isoxazolyl)-1H-indole-3-methanol; m.p. 178° to 180° C.

Following the above procedure and using in place of N,N-dimethyl-2-(3-ethyl-5-methyl-4-isoxazolyl)-3-indoleglyoxylamide an equivalent amount of
(a) N,N-dimethyl-2-(3-ethyl-4-isoxazolyl)-3-indoleglyxoylamide,
(b) N,N-dimethyl-2-(3,5-diethyl-4-isoxazolyl)-3-indoleglyoxylamide,
(c) N,N-dimethyl-2-(3-ethyl-5-isopropyl-4-isoxazolyl)-3-indoleglyoxylamide,
(d) N,N-dimethyl-2-(3-ethyl-5-t-butyl-4-isoxazolyl)-3-indoleglyoxylamide,
(e) N,N-dimethyl-2-(3,5-dimethyl-4-isoxazolyl)-3-indoleglyoxylamide,
(f) N,N-dimethyl-2-(5-methyl-4-isoxazolyl)-3-indoleglyoxylamide,
(g) N,N-dimethyl-2-(5-methyl-3-propyl-4-isoxazolyl)-3-indoleglyoxylamide,
(h) N,N-dimethyl-2-(5-methyl-3-t-butyl-4-isoxazolyl)-3-indoleglyoxylamide,
(i) N,N-dimethyl-2-(5-ethyl-3-methyl-4-isoxazolyl)-3-indoleglyoxylamide,
(j) N,N-dimethyl-2-(3-isopropyl-5-methyl-4-isoxazolyl)-3-indoleglyoxylamide,
(k) 5-fluoro-N,N-dimethyl-2-(3-ethyl-5-methyl-4-isoxazolyl)-3-indoleglyoxylamide,
(l) 5-methyl-N,N-dimethyl-2-(3-ethyl-5-methyl-4-isoxazolyl)-3-indoleglyoxylamide,
(m) 5-methoxy-N,N-dimethyl-2-(3-ethyl-5methyl-4-isoxazolyl)-3-indoleglyoxylamide,
(n) N,N-diethyl-2-(3-ethyl-5-methyl-4-isoxazolyl)-3-indoleglyoxylamide,
(o) 2-(3-ethyl-5-methyl-4-isoxazolyl)-3-indoleglyoxylmorpholide,
(p) 2-(3-ethyl-5-methyl-4-isoxazolyl)-3-indoleglyoxylpyrrolidide,
(q) 2-(3-ethyl-5-methyl-4-isoxazolyl)-3-indoleglyoxylpiperidide,
(r) 5-fluoro-2-(3-ethyl-5-methyl-4-isoxazolyl)-3-indoleglyoxylpyrrolidide,
(s) 5-fluoro-N,N-dimethyl-2-(3,5-dimethyl-4-isoxazolyl)-3-indoleglyoxylamide,
(t) 5-fluoro-N,N-dimethyl-2-(5-ethyl-3-methyl-4-isoxazolyl)-3-indoleglyoxylamide,
(u) 5-fluoro-2-(5-ethyl-3-methyl-4-isoxazolyl)-3-indoleglyoxylpyrrolidide, or
(v) 5-fluoro-2-(3,5-dimethyl-4-isoxazolyl)-3-indoleglyoxylpyrrolidide,
there is obtained
(a) α-(dimethylaminomethyl)-2-(3-ethyl-4isoxazolyl)-1H-indole-3-methanol, m.p. 148° to 150° C.
(b) α-(dimethylaminomethyl)-2-(3,5-diethyl-4-isoxazolyl)-1H-indole-3-methanol, m.p. 148° to 149° C.
(c) α-(dimethylaminomethyl)-2-(3-ethyl-5-isopropyl-4-isoxazolyl)-1H-indole-3-methanol,
(d) α-(dimethylaminomethyl)-2-(3-ethyl-5-t-butyl-4-isoxazolyl)-1H-indole-3methanol,
(e) α-(dimethylaminomethyl)-2-(3,5-dimethyl-4-isoxazolyl)-1H-indole-3-methanol, m.p. 188° to 189° C.
(f) α-(dimethylaminomethyl)-2-(5-methyl-4-isoxazolyl)-1H-indole-3-methanol,
(g) α-(dimethylaminomethyl)-2-(5-methyl-3-propyl-4-isoxazolyl)-1H-indole-3-methanol, m.p. 176° to 178° C.
(h) α-(dimethylaminomethyl)-2-(5-methyl-3-t-butyl-4-isoxazolyl)-1H-indole-3-methanol, m.p. 205° to 206° C.
(i) α-(dimethylaminomethyl)-2-(5-ethyl-3-methyl-4-isoxazolyl)-1H-indole-3-methanol, m.p. 153° to 155° C.
(j) α-(dimethylaminomethyl)-2-(3-isopropyl-5-methyl-4-isoxazolyl)-1H-indole-3-methanol, m.p. 186° to 188° C.
(k) α-(dimethylaminomethyl)-5-fluoro-2-(3-ethyl-5-methyl-4-isoxazolyl)-1H-indole-3-methanol, m.p. 125° to 127° C.
(l) α-(dimethylaminomethyl)-5-methyl-2-(3-ethyl-5-methyl-4-isoxazolyl)-1H-indole-3-methanol,
(m) α-(dimethylaminomethyl)-5-methoxy-2-(3-ethyl-5-methyl-4-isoxazolyl)-1H-indole-3-methanol,
(n) α-(diethylaminomethyl)-2-(3-ethyl-5-methyl-4-isoxazolyl)-1H-indole-3-methanol, m.p. 153° to 154° C.
(o) α-(morpholinomethyl)-2-(3-ethyl-5-methyl-4-isoxazolyl)-1H-indole-3-methanol, m.p. 169° to 171° C.
(p) α-(pyrrolidinomethyl)-2-(3-ethyl-5-methyl-4-isoxazolyl)-1H-indole-3-methanol, m.p. 166° to 168° C.
(q) α-(piperidinomethyl)-2-(3-ethyl-5-methyl-4-isoxazolyl)-1H-indole-3-methanol, m.p. 166° to 167° C.
(r) α-(pyrrolidinomethyl)-5-fluoro-2-(3-ethyl-5-methyl-4-isoxazolyl)-1H-indole-3-methanol, m.p. 159° to 160° C.
(s) α-(dimethylaminomethyl)-5-fluoro-2-(3,5-dimethyl-4-isoxazolyl)-1H-indole-3-methanol, m.p. 175° to 178° C.
(t) α-(dimethylaminomethyl)-5-fluoro-2-(3-methyl-5-ethyl-4-isoxazolyl)-1H-indole-3-methanol, m.p. 79° to 80° C.
(u) α-(pyrrolidinomethyl)-5-fluoro-2-(5-ethyl-3-methyl-4-isoxazolyl)-1H-indole-3-methanol, m.p. 168° to 169° C., or
(v) α-(pyrrolidinomethyl)-5-fluoro-(3,5-dimethyl-4-isoxazolyl)-1H-indole-3-methanol, respectively.

The α-(dimethylaminomethyl)-2-(3-ethyl-5-methyl-4-isoxazolyl)-1H-indole-3-methanol of Example 5 is an effective anti-diabetic agent at a dosage of 200 mg two to four times a day.

The title compound of Example 5 has an $ED_{25}$ of 75.0 mg/kg p.o. in mice as a hypoglycemic agent.

EXAMPLE 6

A preferred process for preparing the compounds of formula (V) wherein $R_5$ represents ethyl in particular the 2-(5-ethyl-3-methyl-4-isoxazolyl)-indole [compound of formula Vb].

A solution of 5 g (0.024 mole) of 2-(3,5-dimethyl-4-isoxazolyl)-indole in 100 ml of dry tetrahydrofuran is cooled to −60° and treated by dropwise addition with 32.4 ml of 1.6 M n-butyllithium in hexane (0.052 mole) maintaining temperature at −60° C. The resulting mixture is then stirred at −60° C. for 30 min. and then treated by dropwise addition of 4.01 g (0.028 mole) of methyl iodide in 10 ml dry tetrahydrofuran. The resulting mixture is stirred at −60° for 4 hours and quenched by the addition of 6 ml saturated ammonium chloride solution. The mixture is then warmed to room temperature and treated with 50 ml of water and extracted with methylene chloride. The organic layers are dried over magnesium sulfate, filtered and evaporated in vacuo. The resulting oil is then purified by filtration through silica gel to give 2-(5-ethyl-3-methyl-4-isoxazolyl)-indole as a viscous oil.

What is claimed is:

1. A pharmaceutical composition useful in treating diabetes as a hypoglycemic agent comprising a compound of the formula:

wherein
$R_1$ represents hydrogen, fluoro, chloro, lower alkyl having 1 to 4 carbon atoms, or lower alkoxy having 1 to 4 carbon atoms, and
$R_2$ represents hydroxy, and
$R_3$ and $R_4$ each independently represent lower alkyl having 1 to 4 carbon atoms, or
$R_3$ and $R_4$ together with N represent wherein
n is 1, 2 or 3, and
$R_5$ and $R_6$ each independently represent hydrogen or lower alkyl having 1 to 4 carbon atoms,
or pharmaceutically acceptable acid addition salt thereof in association with a pharmaceutical carrier or diluent, said compound being present in an amount sufficient to provide a daily dose of 50 to 2000 milligrams of compounds.

2. A pharmaceutical composition according to claim 1 comprising 12.5 to 2000 milligrams per unit dosage.

3. A pharmaceutical composition according to claim 1 comprising 12.5 to 1000 milligrams per unit dosage.

4. A pharmaceutical composition according to claim 1 in which the compound is α-(dimethylaminomethyl)-2-(3-ethyl-5-methyl-4-isoxazolyl)-1H-indole-3-methanol or a pharmaceutically acceptable acid addition salt thereof.

5. A pharmaceutical composition according to claim 1 in which the compound is selected from the group consisting of
(a) α-(dimethylaminomethyl)-2-(3-ethyl-4-isoxazolyl)-1H-indole-3-methanol;
(b) α-(dimethylaminomethyl)-2-(3,5-diethyl-4-isoxazolyl)-1H-indole-3-methanol;
(c) α-(dimethylaminomethyl)-2-(3,5-dimethyl-4-isoxzaolyl)-1H-indole-3-methanol;
(d) α-(dimethylaminomethyl)-2-(5-methyl-3-propyl-4-isoxazolyl)-1H-indole-3-methanol;
(e) α-(dimethylaminomethyl)-2-(5-methyl-3-t-butyl-4-isoxazolyl)-1H-indole-3-methanol;
(f) α-(dimethylaminomethyl)-2-(5-ethyl-3-methyl-4-isoxazolyl)-1H-indole-3-methanol;
(g) α-(dimethylaminomethyl)-2-(3-isopropyl-5-methyl-4-isoxazolyl)-1H-indole-3-methanol;
(h) α-(dimethylaminomethyl)-5-fluoro-2(3-ethyl-5-methyl-4-isoxazolyl)-1H-indole-3-methanol;
(i) α-(diethylaminomethyl)-2-(3-ethyl-5-methyl-4-isoxazolyl)-1H-indole-3-methanol;
(j) α-(morpholinomethyl)-2-(3-ethyl-5-methyl-4-isoxazolyl)-1H-indole-3-methanol;
(k) α-(pyrrolidinomethyl)-2-(3-ethyl-5-methyl-4-isoxazolyl)-1H-indole-3-methanol;
(l) α-(piperidinomethyl)-2-(3-ethyl-5-methyl-4-isoxazolyl)-1H-indole-3-methanol;
(m) α-(pyrrolidinomethyl)-5-fluoro-2-(3-ethyl-5-methyl-4-isoxazolyl)-1H-indole-3-methanol;
(n) α-(dimethylaminomethyl)-5-fluoro-2-(3,5-dimethyl-4-isoxazolyl)-1H-indole-3-methanol;
(o) α-(dimethylaminomethyl)-5-fluoro-2-(3-methyl-5-ethyl-4-isoxazolyl)-1H-indole-3-methanol;
(p) α-(pyrrolidinomethyl)-5-fluoro-2-(5-ethyl-3-methyl-4-isoxazolyl)-1H-indole-3-methanol; or
(q) α-(pyrrolidinomethyl)-5-fluoro-2-(3,5-dimethyl-4-isoxazolyl)-1H-indole-3-methanol
or a pharmaceutically acceptable acid addition salt thereof.

6. A pharmaceutical composition useful in treating diabetes by inhibiting post-prandial hyperglycema comprising a compound of the formula wherein
$R_1$ represents hydrogen, fluoro, chloro, lower alkyl having 1 to 4 carbon atoms, or lower alkoxy having 1 to 4 carbon atoms, and
$R_2$ represents hydroxy, and
$R_3$ and $R_4$ each independently represent lower alkyl having 1 to 4 carbon atoms, or
$R_3$ and $R_4$ together with N represent wherein n is 1, 2 or 3, and R<sub>5</sub> and R<sub>6</sub> each independently represent hydrogen or lower alkyl having 1 to 4 carbon atoms, or a pharmaceutically acceptable acid addition salt thereof in association with a pharmaceutical carrier or diluent, said compound being present in an amount sufficient to provide a daily dose of 25 to 1000 milligrams of compound.

7. A pharmaceutical composition according to claim 6 in unit dosage form for administration 3 times a day.

8. A pharmaceutical composition according to claim 6 in which the compound is α-(dimethylaminomethyl)-2-(3-ethyl-5-methyl-4-isoxazolyl)-1H-indole-3-methanol or a pharmaceutically acceptable acid addition salt thereof.

9. A pharmaceutical composition according to claim 6 in which the compound is selected from the group consisting of (a) α-(dimethylaminomethyl)-2-(3-ethyl-4-isoxazolyl)-1H-indole-3-methanol;
(b) α-(dimethylaminomethyl)-2-(3,5-diethyl-4-isoxazolyl)-1H-indole-3-methanol;
(c) α-(dimethylaminomethyl)-2-(3,5-dimethyl-4-isoxazolyl)-1H-indole-3-methanol;
(d) α-(dimethylaminomethyl)-2-(5-methyl-3-propyl-4-isoxazolyl)-1H-indole-3-methanol;
(e) α-(dimethylaminomethyl)-2-(5-methyl-3-t-butyl-4-isoxazolyl)-1H-indole-3-methanol;
(f) α-(dimethylaminomethyl)-2-(5-ethyl-3-methyl-4-isoxazolyl)-1H-indole-3-methanol;
(g) α-(dimethylaminomethyl)-2-(3-isopropyl-5-methyl-4-isoxazolyl)-1H-indole-3-methanol;
(h) α-(dimethylaminomethyl)-5-fluoro-2-(3-ethyl-5-methyl-4-isoxazolyl)-1H-indole-3-methanol;
(i) α-(diethylminomethyl)-2-(3-ethyl-5-methyl-4-isoxazolyl)-1H-indole-3-methanol;
(j) α-(morpholinomethyl)-2-(3-ethyl-5-methyl-4-isoxazolyl)-1H-indole-3-methanol;
(k) α-(pyrrolidinomethyl)-2-(3-ethyl-5-methyl-4-isoxazolyl)-1H-indole-3-methanol;
(l) α-(piperidinomethyl)-2-(3-ethyl-5-methyl-4-isoxazolyl)-1H-indole-3-methanol;
(m) α-(pyrrolidinomethyl)-5-fluoro-2-(3-ethyl-5-methyl-4-isoxazolyl)-1H-indole-3-methanol;
(n) α-(dimethylaminomethyl)-5-fluoro-2-(3,5-dimethyl-4-isoxazolyl)-1H-indole-3-methanol;
(o) α-(dimethylaminomethyl)-5-fluoro-2-(3-methyl-5-ethyl-4-isoxazolyl)-1H-indole-3-methanol;
(p) α-(pyrrolidinomethyl)-5-fluoro-2-(5-ethyl-3-methyl-4-isoxazolyl)-1H-indole-3-methanol; or
(q) α-(pyrrolidinomethyl)-5-fluoro-2-(3,5-dimethyl-4-isoxazolyl)-1H-indole-3-methanol or a pharmaceutically acceptable acid addition salt thereof.

10. A method of treating diabetes in mammals which comprises administering to a mammal in need of such treatment an anti-diabetes effective amount of a compound of the formula

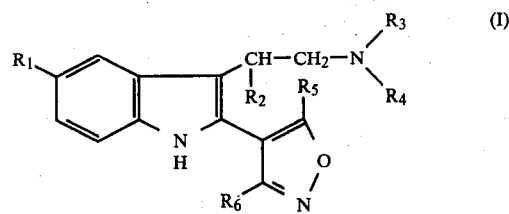

wherein

R<sub>1</sub> represents hydrogen, fluoro, chloro, lower alkyl having 1 to 4 carbon atoms, or lower alkoxy having 1 to 4 carbon atoms, and R<sub>2</sub> represents hydroxy, and R<sub>3</sub> and R<sub>4</sub> each independently represent lower alkyl having 1 to 4 carbon atoms, or R<sub>3</sub> and R<sub>4</sub> together with N represent

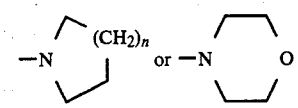

wherein n is 1, 2 or 3, and

R<sub>5</sub> and R<sub>6</sub> each independently represent hydrogen or lower alkyl having 1 to 4 carbon atoms, or a pharmaceutically acceptable acid addition salt thereof.

11. A method according to claim 10 in which 50 to 2000 milligrams of the compound is administered daily as a hypoglycemic agent.

12. A method according to claim 11 in which 12.5 to 2000 milligrams of the compound is administered per unit dose.

13. A method according to claim 11 in which 12.5 to 1000 milligrams of the compound is administered per unit dose.

14. A method according to claim 11 in which the compound is α-(dimethylaminomethyl)-2-(3-ethyl-5-methyl-4-isoxazolyl)-1H-indole-3-methanol or a pharmaceutically acceptable acid addition salt thereof.

15. A method according to claim 11 in which the compound is selected from the group consisting of (a) α-(dimethylaminomethyl)-2-(3-ethyl-4-isoxazolyl)-1H-indole-3-methanol;
(b) α-(dimethylaminomethyl)-2-(3,5-diethyl-4-isoxazolyl)-1H-indole-3-methanol;
(c) α-(dimethylaminomethyl)-2-(3,5-dimethyl-4-isoxazolyl)-1H-indole-3-methanol;
(d) α-(dimethylaminomethyl)-2-(5-methyl-3-propyl-4-isoxazolyl)-1H-indole-3-methanol;
(e) α-(dimethylaminomethyl)-2-(5-methyl-3-t-butyl-4-isoxazolyl)-1H-indole-3-methanol;
(f) α-(dimethylaminomethyl)-2-(5-ethyl-3-methyl-4-isoxazolyl)-1H-indole-3-methanol;
(g) α-(dimethylaminomethyl)-2-(3-isopropyl-5-methyl-4-isoxazolyl)-1H-indole-3-methanol;
(h) α-(dimethylaminomethyl)-5-fluoro-2-(3-ethyl-5-methyl-4-isoxazolyl)-1H-indole-3-methanol;
(i) α-(diethylaminomethyl)-2-(3-ethyl-5-methyl-4-isoxazolyl)-1H-indole-3-methanol;
(j) α-(morpholinomethyl)-2-(3-ethyl-5-methyl-4-isoxazolyl)-1H-indole-3-methanol;
(k) α-(pyrrolidinomethyl)-2-(3-ethyl-5-methyl-4-isoxazolyl)-1H-indole-3-methanol;

(l) α-(piperidinomethyl)-2-(3-ethyl-5-methyl-4-isoxazolyl)-1H-indole-3-methanol;

(m) α-(pyrrolidinomethyl)-5-fluoro-2-(3-ethyl-5-methyl-4-isoxazolyl)-1H-indole-3-methanol;

(n) α-(dimethylaminomethyl)-5-fluoro-2-(3,5-dimethyl-4-isoxazolyl)-1H-indole-3-methanol;

(o) α-(dimethylaminomethyl)-5-fluoro-2-(3-methyl-5-ethyl-4-isoxazolyl)-1H-indole-3-methanol;

(p) α-(pyrrolidinomethyl)-5-fluoro-2-(5-ethyl-3-methyl-4-isoxazolyl)-1H-indole-3-methanol; or (q) α-(pyrrolidinomethyl)-5-fluoro-2-(3,5-dimethyl-4-isoxazolyl)-1H-indole-3-methanol or a pharmaceutically acceptable acid addition salt thereof.

16. A method according to claim 10 in which 25 to 1000 milligrams of the compound is administered daily to inhibit post-prandial hyperglycemia.

17. A method according to claim 16 in which the compound is administered in unit dosage form three times a day.

18. A method according to claim 16 in which the compound is α-(dimethylaminomethyl)-2-(3-ethyl-5-methyl-4-isoxazolyl)-1H-indole-3-methanol or a pharmaceutically acceptable acid addition salt thereof.

19. A method according to claim 16 in which the compound is selected from the group consisting of (a) α-(dimethylaminomethyl)-2-(3-ethyl-4-isoxazolyl)-1H-indole-3-methanol;

(b) α-(dimethylaminomethyl)-2-(3,5-diethyl-4-isoxazolyl)-1H-indole-3-methanol;

(c) α-(dimethylaminomethyl)-2-(3,5-diemthyl-4-isoxzaolyl)-1H-indole-3-methanol;

(d) α-(dimethylaminomethyl)-2-(5-methyl-3-propyl-4-isoxazolyl)-1H-indole-3-methanol;

(e) α-(dimethylaminomethyl)-2-(5-methyl-3-t-butyl-4-isoxazolyl)-1H-indole-3-methanol;

(f) α-(dimethylaminomethyl)-2-(5-ethyl-3-methyl-4-isoxazolyl)-1H-indole-3-methanol;

(g) α-(dimethylaminomethyl)-2-(3-isopropyl-5-methyl-4-isoxazolyl)-1H-indole-3-methanol;

(h) α-(dimethylaminomethyl)-5-fluoro-2-(3-ethyl-5-methyl-4-isoxazolyl)-1H-indole-3-methanol;

(i) α-(diethylaminomethyl)-2-(3-ethyl-5-methyl-4-isoxazolyl)-1H-indole-3-methanol;

(j) α-(morpholinomethyl)-2-(3-ethyl-5-methyl-4-isoxazolyl)-1H-indole-3-methanol;

(k) α-(pyrrolidinomethyl)-2-(3-ethyl-5-methyl-4-isoxazolyl)-1H-indole-3-methanol;

(l) α-(piperidinomethyl)-2-(3-ethyl-5-methyl-4-isoxazolyl)-1H-indole-3-methanol;

(m) α-(pyrrolidinomethyl)-5-fluoro-2-(3-ethyl-5-methyl-4-isoxazolyl)-1H-indole-3-methanol;

(n) α-(dimethylaminomethyl)-5-fluoro-2-(3,5-dimethyl-4-isoxazolyl)-1H-indole-3-methanol;

(o) α-(dimethylaminomethyl)-5-fluoro-2-(3-methyl-5-ethyl-4-isoxazolyl)-1H-indole-3-methanol;

(p) α-(pyrrodidinomethyl)-5-fluoro-2-(5-ethyl-3-methyl-4-isoxazolyl)-1H-indole-3-methanol; or (q) α-(pyrrolidinomethyl)-5-fluoro-2-(3,5-dimethyl-4-isoxazolyl)-1H-indole-3-methanol or a pharmaceutically acceptable acid addition salt thereof.

* * * * *